(12) United States Patent
Patel et al.

(10) Patent No.: US 6,682,534 B2
(45) Date of Patent: Jan. 27, 2004

(54) ENDPLATE PREPARATION INSTRUMENT AND ASSOCIATED METHOD

(75) Inventors: Tushar Ch. Patel, Potomac, MD (US); Morris D. Cesarone, Linwood, MA (US); Carl G. Souza, Dighton, MA (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 09/921,055

(22) Filed: Aug. 2, 2001

(65) Prior Publication Data

US 2003/0028190 A1 Feb. 6, 2003

(51) Int. Cl.$^7$ ................................................ A61B 17/56
(52) U.S. Cl. .......................................... 606/79; 606/90
(58) Field of Search ........................ 606/79, 80, 84–86, 606/90, 96, 99; 407/56–61

(56) References Cited

U.S. PATENT DOCUMENTS

| | | | | |
|---|---|---|---|---|
| 3,554,192 A | * | 1/1971 | Isberner | 606/80 |
| 4,988,241 A | * | 1/1991 | Colligan | 407/51 |
| 5,015,247 A | | 5/1991 | Michelson | 606/61 |
| 5,190,548 A | * | 3/1993 | Davis | 606/80 |
| 5,484,437 A | | 1/1996 | Michelson | 606/61 |
| 5,505,732 A | | 4/1996 | Michelson | 606/61 |
| 5,720,748 A | | 2/1998 | Kuslich et al. | 606/80 |
| 5,792,044 A | | 8/1998 | Foley et al. | 600/114 |
| 5,797,909 A | | 8/1998 | Michelson | 606/61 |
| 5,902,231 A | | 5/1999 | Foley et al. | 600/114 |
| 5,954,635 A | | 9/1999 | Foley et al. | 600/114 |
| 6,004,326 A | * | 12/1999 | Castro et al. | 606/99 |
| 6,007,487 A | | 12/1999 | Foley et al. | 600/235 |
| 6,080,155 A | | 6/2000 | Michelson | 606/61 |
| 6,083,225 A | * | 7/2000 | Winslow et al. | 606/61 |
| 6,096,038 A | | 8/2000 | Michelson | 606/61 |
| 6,152,871 A | | 11/2000 | Foley et al. | 600/114 |
| 6,159,214 A | | 12/2000 | Michelson | 606/80 |
| 6,162,170 A | | 12/2000 | Foley et al. | 600/114 |
| 6,174,311 B1 | | 1/2001 | Branch et al. | 606/61 |
| 6,540,753 B2 | * | 4/2003 | Cohen | 606/99 |
| 2001/0000532 A1 | | 4/2001 | Michelson | |

FOREIGN PATENT DOCUMENTS

EP    1129688   *  5/2001   ........... A61B/17/17

* cited by examiner

Primary Examiner—Eduardo C. Robert
Assistant Examiner—Michael B. Priddy
(74) Attorney, Agent, or Firm—Nutter, McClennen & Fish LLP

(57) ABSTRACT

A surgical bone preparation instrument that is effective to prepare the surface of adjacent bone structures, and more particularly to remove a predetermined portion of bone from the vertebral endplates of adjacent vertebral bodies, is provided. In general, the surgical bone preparation instrument includes a housing member having an inner lumen formed therein, and an elongate member rotatably disposable within the housing member. The housing member can include a distractor member adapted to be disposed between adjacent bone structures, and optionally a rotation limiting element, and/or a stop member. In use, the elongate member is rotated with respect to the housing, thereby causing the cutting element to penetrate and remove bone from the adjacent bone structures.

48 Claims, 6 Drawing Sheets

ENDPLATE PREPARATION INSTRUMENT AND ASSOCIATED METHOD

FIELD OF THE INVENTION

The present invention relates to instruments and methods for preparing adjacent bone structures, and more particularly, to instruments and methods for preparing adjacent vertebral endplates prior to a spinal fusion procedure.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

In general, the ability to achieve bone fusion appears to be related to certain factors, such as the quality and quantity of bone graft material present, the surface area available for the fusion to occur over, and the stability of the construct being fused. The fusion cage and/or bone graft should, for example, occupy a significant portion of the disc space to provide a large surface area over which fusion can occur, and should contour the vertebral endplates adjacent the disc space to provide stability and further promote fusion. The fusion cage and/or bone graft used for the purpose of interbody fusion, however, can not always be shaped to precisely fit the complex contours of the vertebral endplates adjacent the disc space. Accordingly, rather than shaping the fusion cage to contour the disc space, procedures have been developed for removing at least a portion of the outermost layer of the vertebral endplates. This is effective to cause bleeding to occur, and thereby to encourage the fusion and invoke the healing process of the bone.

Since the vertebral endplates are generally quite strong, it is desirable to preserve this structure even while removing portions of the bone. In the past, anterior interbody fusion would be performed by removing at least a portion of the intervertebral disc and then utilizing hand held instruments including, for example, osteotomes, chisels, curettes, rongeurs, and burrs to scrape and shape the vertebral endplates and vertebral bone stock. Such operations would be performed generally by working on one vertebra at a time, independent of the position of the adjacent vertebra.

Endplate preparation procedures can present the surgeon with several challenges. For example, the vertebral endplates should be prepared to match the implant to provide the greatest possible interface congruity between the endplates and the implant, as well as provide for the optimal contact surface, enhanced fusion area, and enhanced graft and construct stability. In order to achieve this, the amount of bone removed must be to a specified depth and width. Excess removal or penetration of the vertebral endplate can result in a weakening of the structural integrity of the vertebrae, thereby potentially causing the vertebral bodies to collapse around the fusion implant. Conversely, where an insufficient amount of bone is removed, blood flow may be very limited thereby hindering fusion of the implant to the vertebrae. This could potentially result in misalignment of the implant due to shifting.

Accordingly, there is a need for instruments and methods for the safe and effective preparation of adjacent vertebral endplates prior to a spinal fusion procedure.

SUMMARY OF THE INVENTION

The present invention provides a surgical bone preparation instrument useful during interbody fusion procedures, and methods of use thereof. The surgical bone preparation instrument is effective to remove a desired portion of bone from adjacent bone structures, such as vertebral endplates, to allow a sufficient amount of blood to flow to the implant, while maintaining the structural integrity of the vertebrae.

In general, the surgical bone preparation instrument includes a housing or sleeve member having an inner lumen or bore formed between a proximal end and a distal end. At least one distractor member protrudes distally from the distal end of the housing member and is adapted to be disposed between adjacent bone structures. The instrument further includes an elongate member, or rotatable cutting member, having a proximal end and a distal end. The proximal end of the elongate member can include a gripping surface, such as a handle, and the distal end of the elongate member includes a cutting element. The elongate member is adapted to be at least partially disposed within the inner lumen of the housing, such that the cutting element is positioned proximate to the distractor member. In use, the elongate member is rotated with respect to the housing, thereby causing the cutting element to penetrate and remove bone from the adjacent bone structures.

In one embodiment, the cutting member includes first and second opposed blade members effective to remove a portion of a surface of a bone structure upon rotation of the elongate member. The blade members are longitudinally oriented and include distal and proximal ends with a cutting surface extending therebetween. The cutting surface of each blade member can include first and second opposed leading edges which are effective to remove a portion of bone upon rotation of the elongate member in both a first direction and a second, opposite direction. The size, shape, and position of the blade members can be adapted to remove a specific region and amount of bone from the vertebral endplates. For example, the first blade member can be disposed distal of the second blade member to remove diametrically opposed regions of bone from the endplates.

In another embodiment, the instrument can include a rotation limiting element which defines a cutting path for the cutting member. The rotation limiting element can be formed from a slot disposed in the housing and extending over a portion of a circumference of the housing. An engaging element, such as a pin member, can be disposed on the rotatable cutting member such that the pin member is adapted to be disposed within the slot in the housing. In use, the shape of the slot defines a cutting path extending over a portion of the circumference of the sleeve member. For example, where the slot extends over 90° of the circumference of the housing, the elongate member can be rotated 90° in a first direction, and 90° in a second, opposite direction thereby causing the first blade member to remove bone from a first vertebral endplate, and the second blade member to remove bone from a second, adjacent vertebral endplate.

In yet another embodiment, the housing component can include a stop member effective to prevent the housing from entering a space between adjacent bone structures. By way of non-limiting example, the stop member can be formed from a flange or shoulder that extends radially outward from the housing and is oriented substantially perpendicular to a longitudinal axis of the instrument.

In order to prepare adjacent bone structures, and more specifically the endplates of adjacent vertebral bodies, the distractor of the surgical bone preparation instrument is inserted between the bone structures to separate the adjacent vertebrae. The elongate member is then rotated, thereby causing the cutting element to remove a portion of bone from the endplate of each vertebra.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a surgical bone preparation instrument that is effective to prepare the surface of adjacent bone structures, and more particularly to remove a predetermined portion of bone from the vertebral endplates of adjacent vertebral bodies to expose the nucleus of the vertebral body. The removed portion of the endplates allows a sufficient amount of blood to flow therethrough and into an implant subsequently positioned between the adjacent vertebrae, thereby enhancing bone growth and facilitating more rapid and secure fusion of the implant with the adjacent vertebrae.

Figure 1:
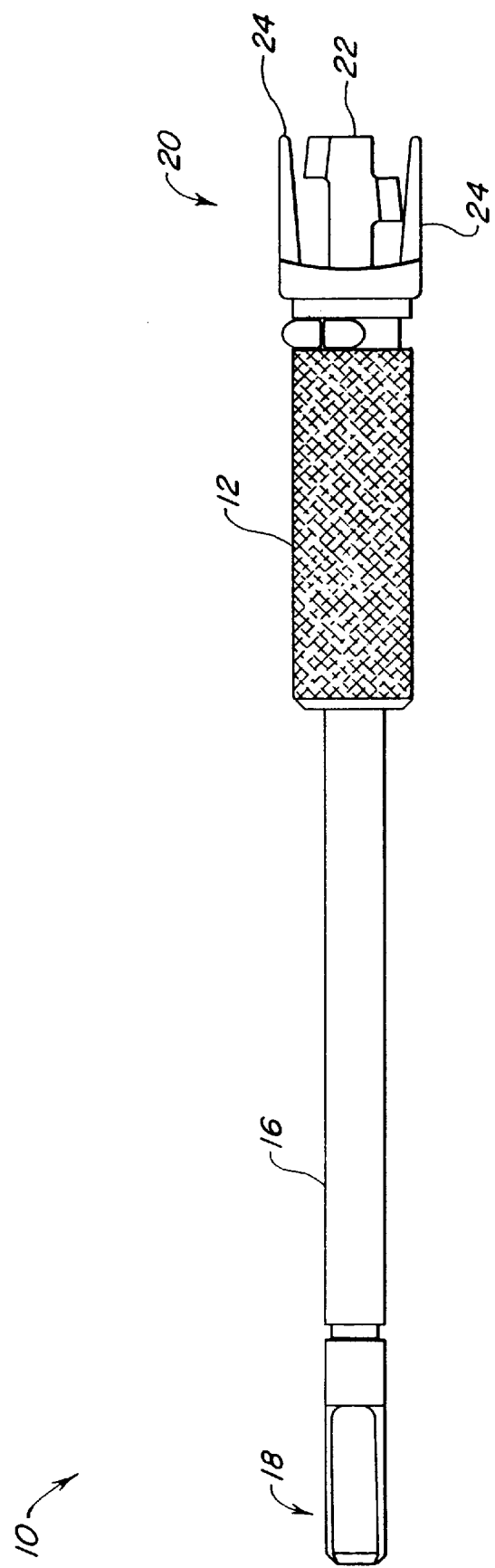
FIG. 1 is a side view of a surgical bone preparation instrument having a housing and an elongate member according to one embodiment of the present invention.

Referring to FIG. 1, the bone preparation instrument 10 according to the present invention generally includes two components: a housing component 12 having an inner lumen 14 (FIG. 2) formed therein, and an elongate member 16 at least partially and rotatably disposed within the inner lumen 14 of the housing 12. The housing 12 can optionally include at least one distractor member 24 adapted to be disposed between adjacent bone structures, and the elongate member 16 can include at least one cutting element 22 positioned between the distractor member 24 and effective to remove portions of adjacent bone structures.

Figure 2:
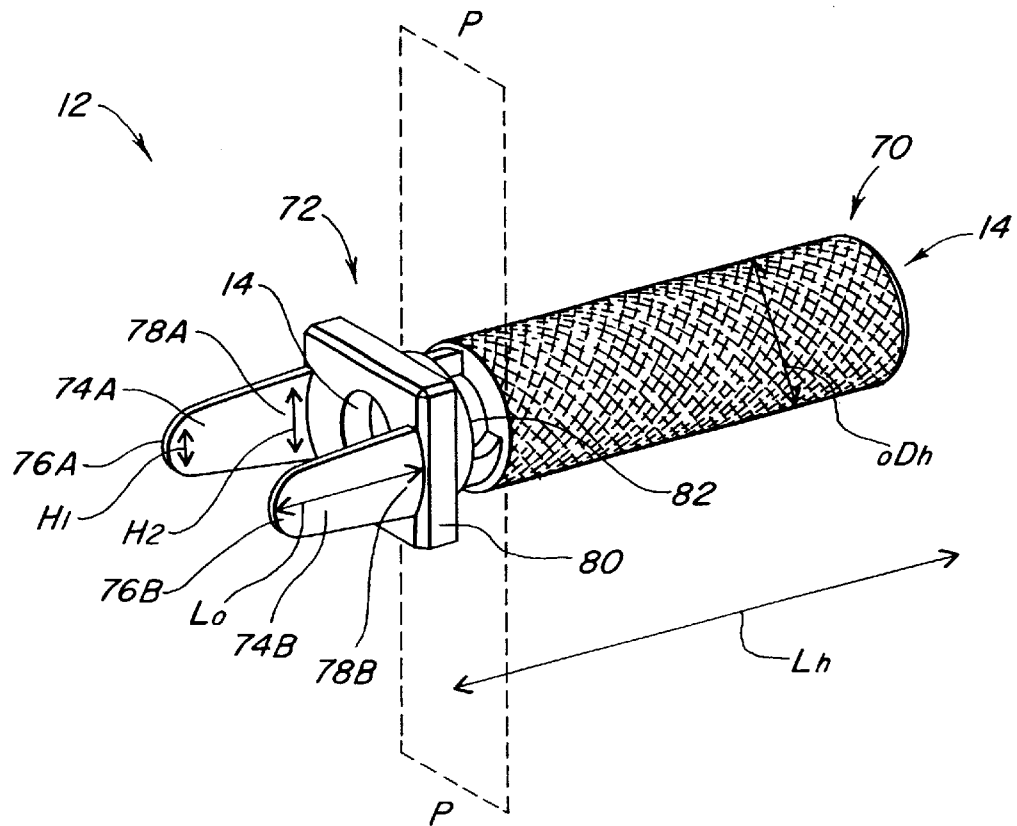
FIG. 2 is a side perspective view of the housing member shown in FIG. 1.

The housing component 12, which is adapted to receive a portion of the elongate member 16, is shown in more detail in FIG. 2, and includes a proximal end 70, a distal end 72, and an inner lumen 14 or bore extending therebetween. The housing component 12 can have a variety of shapes, but is preferably cylindrical in shape and has an outer diameter $oD_h$, inner diameter $iD_h$ (FIG. 4), and length $L_h$. The outer diameter $oD_h$, inner diameter $iD_h$, and length $L_h$ can vary, but preferably the outer diameter $oD_h$ is between about 6 mm and 16 mm, the inner diameter $iD_h$ is between about 3 mm and 8 mm, and the length $L_h$ is between about 20 mm and 60 mm. The housing component 12 can optionally include a distractor member 74 protruding distally from the distal end 72, a stop member 80 formed on the distal end 72, and/or a cutting template 82 for limiting the rotation of the elongate member 16.

Figure 3:
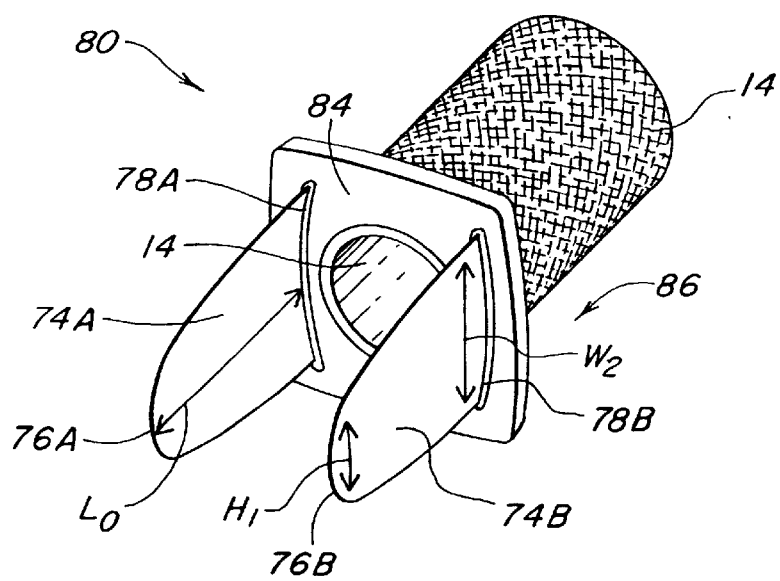
FIG. 3 is a front perspective view of the housing member shown in FIG. 1.

The distractor member 74 is effective to separate and position adjacent bone structures, and can be mated to or formed integrally with the housing component 12. The distractor member 74 can have a variety of shapes and sizes. In one embodiment, as shown in FIGS. 2 and 3, the distractor member 74 includes first and second opposed members 74A, 74B adapted to be disposed between adjacent bone structures, e.g. vertebral bodies. Each opposed member 74A, 74B includes a leading, distal end 76A, 76B and a proximal end 78A, 78B mated the stop member 80 and/or housing component 12. The leading, distal ends 76A, 76B can be substantially bullet-shaped to facilitate insertion of the distractor member 74 between two adjacent vertebral bodies. The opposed members 74A, 74B can optionally be curved inward along the length $L_o$ to contour the circumferential shape of the housing component 12.

The opposed members 74A, 74B can have a variety of shapes and sizes, and can be adapted to separate adjacent vertebrae by a predetermined distance. While the shape and size of the opposed members 74A, 74B can vary, preferably, the distal end 76B of each opposed member 74A, 74B has a height $H_1$ that is less a height $H_2$ of the proximal end 78A, 78B, thereby forming a distal taper. The height $H_1, H_2$ of the opposed members 74A, 74B can be adjusted based on the intended use, e.g. the size of the space between the adjacent vertebrae, but preferably width $H_1$ is between about 3 mm and 12 mm, and more preferably is about 5 mm, and width $H_2$ is between about 5 mm and 9 mm, and more preferably is about 8 mm. The length $L_o$ of each opposed member 74A, 74B will also vary depending on the intended use, however, the length $L_o$ is preferably between about 33 mm and 63 mm. In use, the distal taper of the opposed members 74A, 74B is effective to separate the adjacent vertebrae as the instrument 10 is inserted into the vertebral disc space.

The stop member 80 can be disposed between or formed around the opposed members 74A, 74B and the housing component 12, and is effective to limit penetration of the housing component 12 between the adjacent vertebral bodies. While the stop member 80 can have a variety of shapes, in one embodiment shown in FIG. 3 the stop member is formed from a flange member that is oriented substantially perpendicular to the longitudinal axis L of the elongate member 16 and extends radially outward from the distal end 72 of the housing component 12. The stop member 80 can have any shape, including rectangular, square or circular, and can extend around the entire circumference of the housing component 12 or can be mated to or formed integrally with particular portions of the housing component 12. As shown in FIG. 3, the stop member 80 can include a concave distal surface 84 and a convex proximal surface 86 (not shown) for conforming to the anterior or posterior side of the vertebral bodies. While FIGS. 2 and 3 illustrate one particular embodiment of a stop member 80, a person having ordinary skill in the art will appreciate that a variety of different stop members 80 can be used to prevent penetration of the housing component 12 into the vertebral space. By way of non-limiting example, the housing component 12 can include one or more surface protrusions (e.g., spike members, not shown) extending outward from the distal end 72 and adapted to penetrate the posterior or anterior surface of the vertebral body(s). The surface protrusions are also effective to prevent rotation of the housing component 12 with respect to the elongate member 16.

Figure 4:
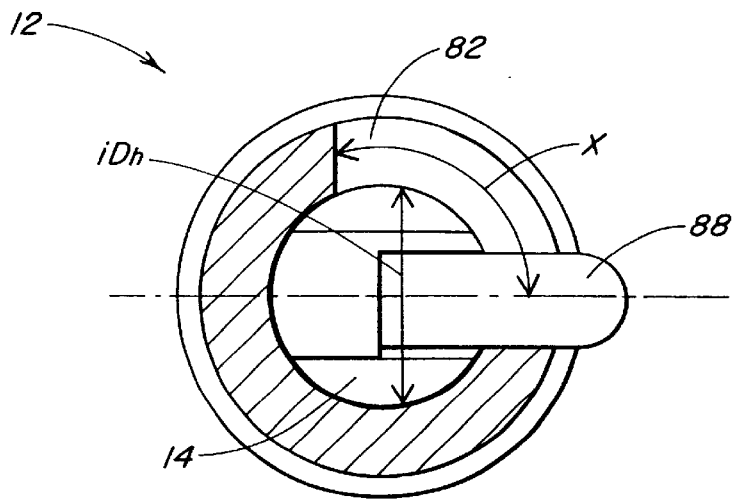
FIG. 4 is a cross-sectional view of the housing member shown in FIG. 2 taken across plane P—P.

FIG. 4 illustrates another embodiment of housing component 12 having a cutting template 82 effective to limit rotation of the elongate member 16. The cutting template 82 is in the form of a circumferential slot formed in the housing component 12 and extending over a portion of the circumference of the housing component 12. The size and shape of the slot defines a cutting path for the cutting element 22 of the elongate member 16. Preferably, the cutting path X extends between about 80° and 120° around the circumference of the sleeve member, and more preferably extends over 90° (FIG. 4) of the circumference of the sleeve member.

In order to limit rotation of the elongate member 16, an engaging member 88 adapted to extend into the slot 82 can be mated to or formed in the elongate member 16. The engaging member 88, shown in FIG. 4, can be, for example, a pin or similar type of structure protruding from the elongate member 16, preferably in a direction perpendicular to a longitudinal axis L of the instrument 10. The engaging member 88 can be removably attached to the elongate member 16 to allow for removal and replacement of the elongate member 16 from the housing component 12. This will allow the surgeon to select from a variety of different housing components 12 having different sized distractors 24, and different elongate members 16 having different sized cutting elements 22. The position of the engaging member 88 along the longitudinal axis L of the elongate member 16 can be adjusted depending on the desired position of the cutting element 22 with respect to the distractor member 24. Referring back to FIG. 1, in one embodiment the engaging member 88 is positioned to cause the distal end 20 of the elongate member 16 to extend from the distal end 72 of the housing component 12.

While the present invention describes a pin and slot-type arrangement, a person having ordinary skill in the art will appreciate that a variety of different rotation limiting elements can be used, such as, for example, a tongue and groove joint, a dove tail connection, or similar type of arrangement.

Figure 5:
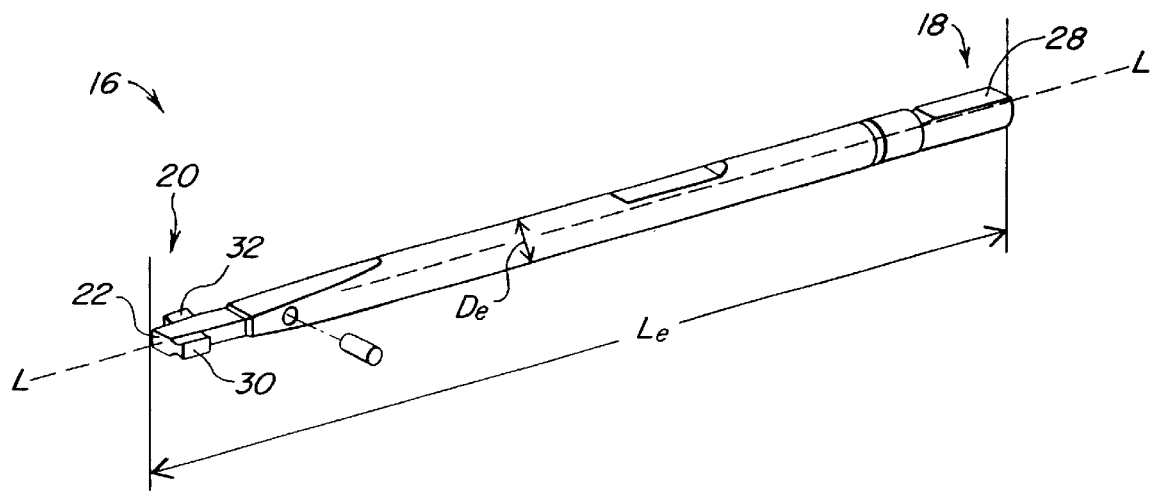
FIG. 5 is a side perspective view of the elongate member shown in FIG. 1 having a cutting element formed on the distal end.

The elongate member 16, shown in FIG. 5, is adapted to be at least partially disposed within the inner lumen of the housing component 12. As shown, the elongate member can have a generally cylindrical shape and includes a proximal end 18 and a distal end 20. The body of the elongate member 16 is preferably rigid and extends along a longitudinal axis L. The diameter $D_e$ of the elongate member 16 can vary along the length $L_e$ of the elongate member 16, but is preferably adapted to fit within the inner lumen of the housing such that the elongate member 16 can be rotated along the longitudinal axis L. In a preferred embodiment, the elongate member has a diameter $D_e$ between about 3 mm and 8 mm, and has a length $L_e$ between about 100 mm and 200 mm. A person having ordinary skill in the art will appreciate that the elongate member 16 can have a variety of shapes and sizes.

The proximal end 18 of the elongate member 16 can include a gripping surface 28 or handle for grasping and rotating the elongate member 16. In one embodiment, the gripping surface 28 can be a knurled surface to facilitate manual rotation of the elongate member. Alternatively, or in addition, the gripping surface 28 can be adapted to mate with a driver device effective to rotate the elongate member. A person having ordinary skill in the art will readily appreciate that the handle can have a variety of shapes and sizes, and devices known in the art for rotating the elongate member can be mated to or disposed within the handle.

The distal end 20 of the elongate member 16 includes a cutting element 22 which is effective to remove portions of adjacent bone structures, such as adjacent vertebrae. The cutting element 22 can include first and second blade members 30, 32 mated to or formed integrally with the elongate member 16. The shape, size, and position of each blade member 30, 32 can be adapted based on the intended use.

Figure 6:
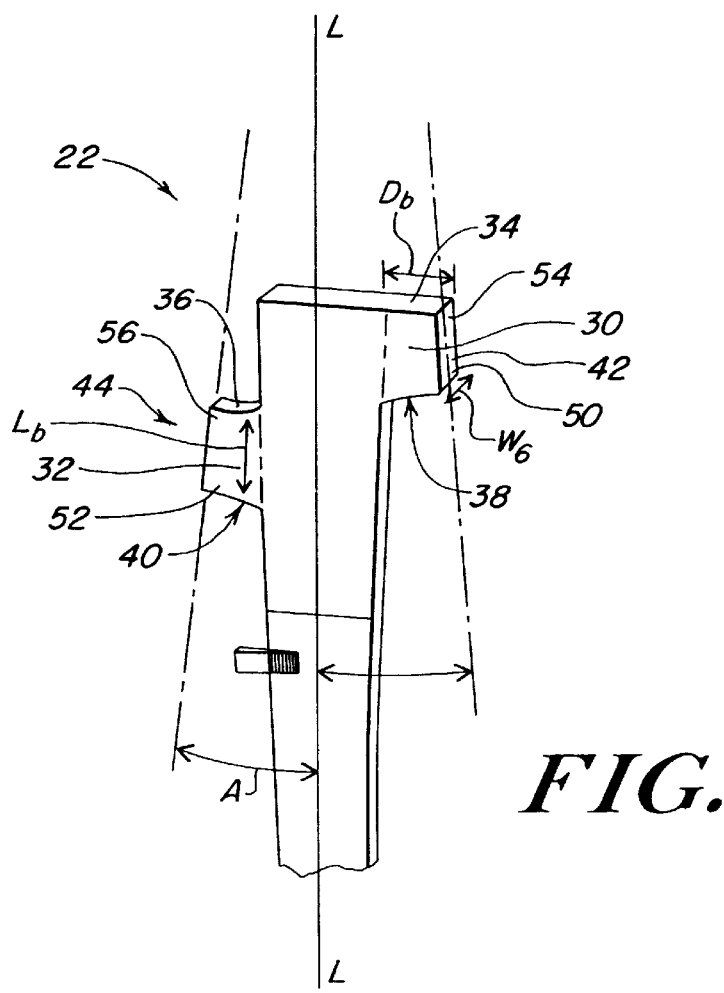
FIG. 6 is a side exploded view of the cutting element shown in FIG. 5.

As shown in FIGS. 5 and 6, the blade members 30, 32 are generally rectangular in shape and include a distal end 34, 36, a proximal end 38, 40, and a cutting surface 42, 44 that extends between the proximal and distal ends. The cutting surface 42, 44 of each blade member 30, 32 can be shaped to match the orientation of the vertebral endplate on which the instrument 10 is intended to be used. For example, the cutting surfaces 42, 44 can be convex or concave, or can have an irregular shape adapted to match specific vertebral endplates.

In the embodiment illustrated in FIG. 6, each cutting surface 42, 44 is angularly oriented such that a proximal portion 50, 52 of the cutting surface 42, 44 is disposed at a greater distance from the longitudinal axis L than a distal portion 54, 56 of the cutting surface 42, 44. This is particularly useful for preparing adjacent vertebrae located along the lower portion of the spinal column since the vertebral bodies are disposed at a greater angle with respect to one another. In a preferred embodiment, each cutting surface 42, 44 is disposed at an angle A from the longitudinal axis L between about 1° and 5°, and preferably at an angle A of about 3.5°. The embodiment shown in FIG. 6 is adapted for use with an anterior-surgical approach. A person having ordinary skill in the art will appreciate that other surgical approaches can be used, and therefore the shape and angle of the cutting surfaces can be adapted accordingly. For example, where a posterior-surgical approach is used, the distal portion of each cutting surface can be disposed at a greater distance from the longitudinal axis than the proximal portion of each cutting surface.

Figure 7:
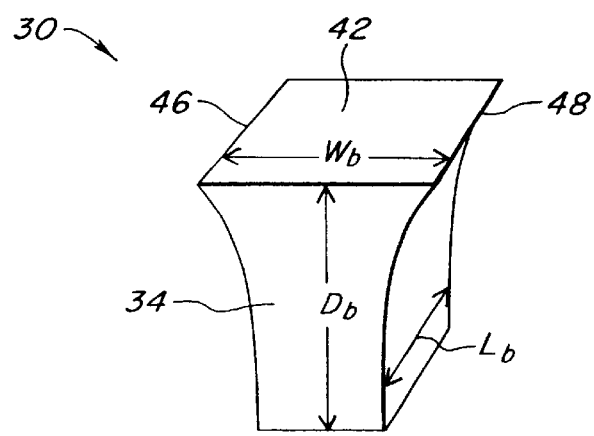
FIG. 7 is an exploded view of a portion of the cutting element shown in FIG. 5.

The cutting surface 42, 44 of each blade member 30, 32 can also be adapted to remove bone upon rotation of the elongate member in both a first direction, and in a second, opposite direction. Referring to FIG. 7, blade member 30 is shown having a distal surface 42 with first and second opposed leading edges 46, 48. The leading edges 46, 48 extend outward from the distal surface 42 to form a substantially sharpened edge effective to penetrate and remove a portion of the vertebral endplate upon rotation of the elongate member 16 in both a first direction and in a second, opposite direction.

The size of each blade member 30, 32 can also vary, but preferably each blade member 30, 32 is disposed radially outward from the elongate member 16 at a predetermined distance $D_b$ (FIG. 6), which extends from the elongate member 16 to the distal surface 42, 44. The distance $D_b$ can vary along a length $L_b$ of each distal surface 42, 44 and is determinative of the amount of bone to be removed from each endplate. The distance $D_b$ is preferably between about 1 mm and 5 mm, and more preferably is about 2 mm. The longitudinal length $L_b$ and width $W_b$ of the blade members 30, 32 can also vary depending on the intended use. Preferably, each cutting surface 42, 44 has a width $W_b$ between about 2 mm and 4 mm, and more preferably about 3 mm. The length $L_b$ of the blade members 30, 32 will vary based on the size of the vertebral endplate to be prepared, but is preferably between about 2 mm and 6 mm, and more preferably about 5 mm. A person having ordinary skill in the art will appreciate that the length $L_b$, width $W_b$, and distance $D_b$ can be adapted to removed a predetermined amount of bone from each endplate. Preferably, the blade members 30, 32 are adapted to remove between about 10% and 50% of bone from each endplate, and more preferably about 25% of bone from each endplate.

Figure 8:
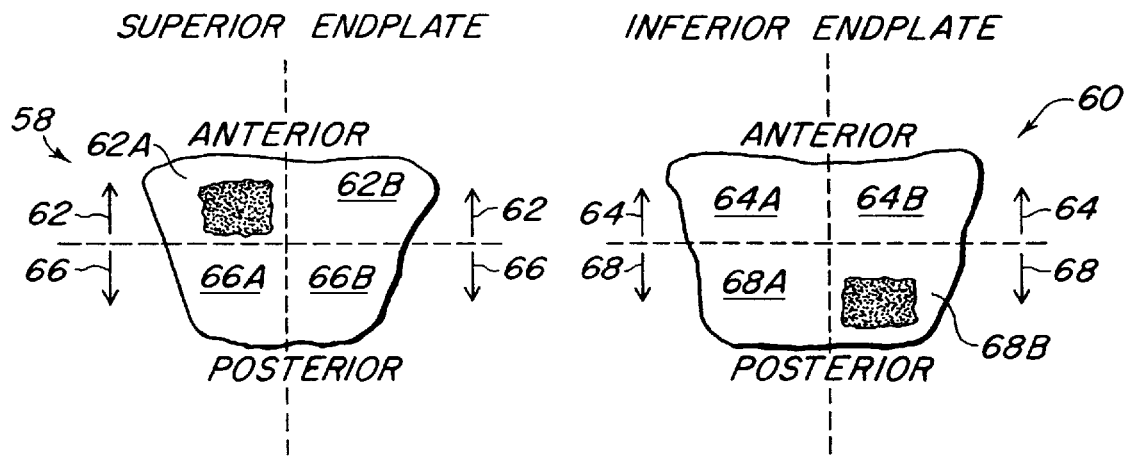
FIG. 8 is an illustration of two adjacent vertebral endplates having removed portions of bone.

While the size and shape of the blade members 30, 32 is determinative of the amount of bone to be removed, the position of the blade members 30, 32 along the longitudinal axis L of the elongate member 16, as well as the degree of rotation of the elongate member 16, is determinative of the exact location of bone to be removed. For illustration purposes, superior and inferior endplates 58, 60 of adjacent vertebral bodies are shown in FIG. 8. Each endplate 58, 60 includes an anterior region 62, 64 having first and second lateral halves 62A, 62B, 64A, 64B, and a posterior region 66, 68 having first and second lateral halves 66A, 66B, 68A, 68B, respectively. The blade members 30, 32 can be adapted to remove bone in one or more regions of each vertebral endplate.

By way of non-limiting example, the first blade member can be disposed distal of and offset from the second blade member 32 (FIG. 1) to remove diagonally opposed regions of bone from adjacent vertebral endplates. Assuming an anterior surgical approach is used, where the first blade member 30 is disposed distally to the second blade member 32, the first blade member 30 will remove a portion of bone from the posterior region 68 of one of the superior or inferior endplates 58, 60, and the second blade member 32 will remove a portion of bone from the anterior region 62 of the opposed endplate 58, 60. Thus, the removed portions of bone from the endplates of the vertebral bodies are diagonally opposed. This is particularly important to maintain the structural integrity of the vertebrae. In a preferred embodiment, the distal end 36 of the second blade member 32 is disposed proximal of the distal end 34 of the first blade member 30. As a result, the removed portions of bone from the endplates of the vertebral bodies are non-contacting or non-adjacent.

By varying the degree of rotation, e.g. with the rotation limiting element or cutting template 82, the amount and region of bone removed from the anterior or posterior region of each endplate can further be adjusted. For example, where the elongate member 16 is rotated 180° in a first direction, and then 180° in a second, opposite direction, the first blade member 30 will remove bone from only one of the two adjacent endplates 58, 60, and the second blade member 32 will only remove bone from the opposed endplate. Alternatively, where the elongate member 16 is rotated 360° in a first direction, the first and second blade members 30, 32 will remove bone from each endplate 58, 60.

In a preferred embodiment, the elongate member 16 is rotated only 90° in a first direction, and 90° in a second, opposite direction. As a result, only a portion of bone from part of the anterior 62, 62 or posterior 66, 68 region of each endplate 58, 60 is removed. As shown in FIG. 8, the elongate member 16 is rotated to cause the first blade member 30 to remove a portion of bone from the second lateral half 68B of the posterior region 68 of the inferior endplate 60, and the second blade member 32 to remove a portion of bone from the first lateral half 62A of the anterior region 62 of the superior endplate 58.

Figure 9:
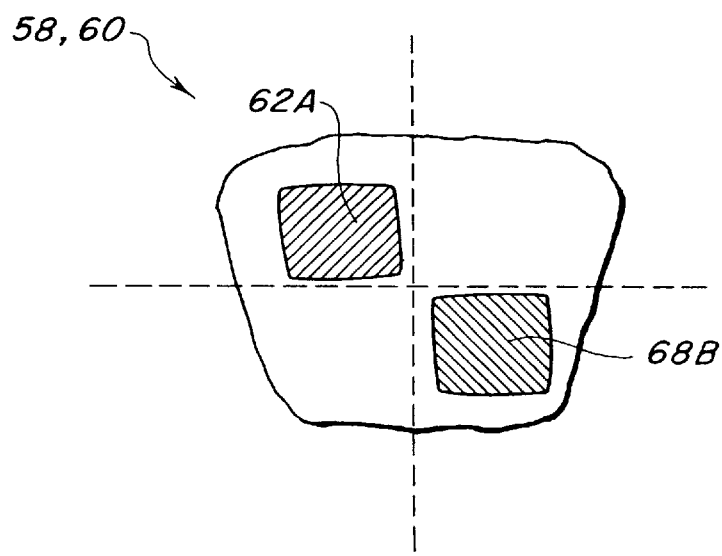
FIG. 9 is an illustration of the vertebral endplates shown in FIG. 8 positioned adjacent one another.

The effect of rotating the elongate member 16 only 90° in each of a first direction and a second, opposite direction is shown in FIG. 9, which illustrates a top view of the endplates 58, 60 disposed adjacent to one another. As shown, the portion of removed bone 62A from the superior endplate 58 is disposed diagonally across a quadrant from the portion of removed bone 68B from the inferior endplate 60. Only about 25% of bone from each endplate 58, 60 is removed. As a result, the annulus of the vertebrae is exposed to allow blood to flow therethrough, yet the structural integrity of each endplate 58, 60 is maintained. Furthermore, the weight bearing load of each endplate on the implant (not shown) is distributed across the surface area of the endplates 58, 60, thereby reducing the risk of the vertebral bodies collapsing around the implant.

Figure 10:
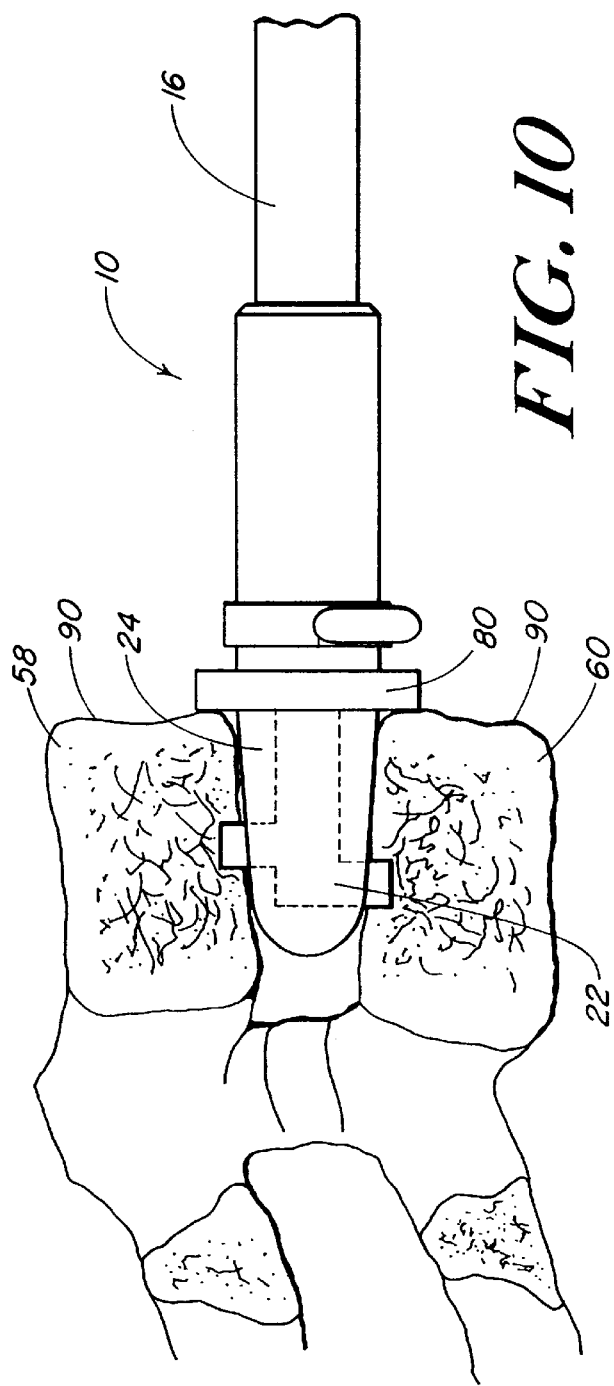
FIG. 10 is a side view illustration of the surgical bone preparation instrument shown in FIG. 1 positioned between adjacent vertebral structures.
Figure 11:
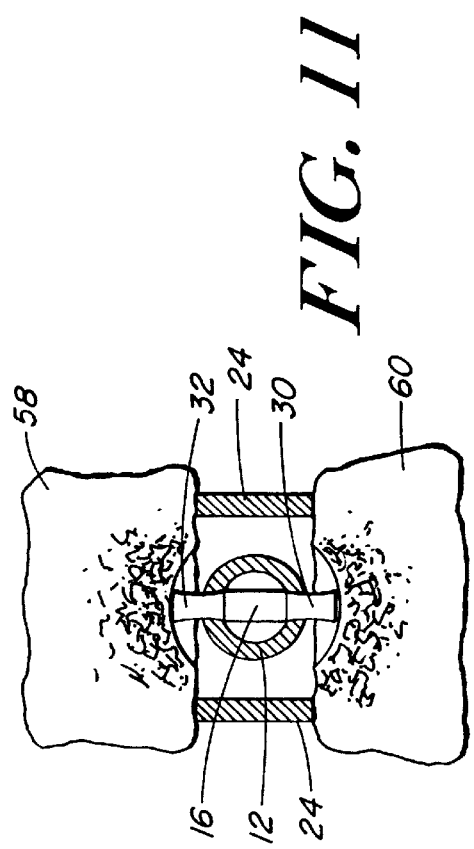
FIG. 11 is an anterior or posterior illustration of the surgical bone preparation instrument shown in FIG. 1 having first and second blade members penetrating adjacent vertebral bodies.

In use, the surgical bone preparation instrument according to the present invention is effective for preparing adjacent bone structures, but is preferably used for preparing endplates of adjacent vertebral bodies. In general, once the disc between two adjacent vertebrae 58, 60 is removed, the instrument 10 is inserted between the vertebrae 58, 60, as shown in FIG. 10. The distractor member 24 is used to separate the vertebrae 58, 60 and position the cutting element 22 between the vertebral endplates. The stop member 80 will abut the exterior surface 90 of the vertebrae 58, 60, thereby preventing over insertion of the instrument 10. Once fully inserted, the elongate member 16 is rotated to remove a portion of bone from each endplate 58, 60, as shown in FIG. 11.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical bone preparation instrument, comprising:
   a sleeve member having a proximal end, a distal end, and an inner lumen formed therein, the sleeve member having at least one distractor member protruding distally from the distal end and adapted to be disposed between adjacent bone structures; and
   an elongate member at least partially rotatably disposed within the sleeve member, the elongate member having a proximal end and a distal end with first and second blade members disposed on a portion of the distal end, each of the first and second blade members having a longitudinally oriented cutting surface formed thereon.

2. The surgical bone preparation instrument of claim 1, wherein the first and second blade members each have a distal end and a proximal end with the cutting surface extending therebetween, the distal end of the second blade member being disposed proximal of the distal end of the first blade member.

3. The surgical bone preparation instrument of claim 2, wherein the proximal end of the first blade member is disposed distal of the distal end of the second blade member.

4. The surgical bone preparation instrument of claim 1, wherein the first and second blade members each have a distal end and a proximal end with the cutting surface extending therebetween, each cutting surface having first and second opposed leading edges adapted to remove a portion of a surface of a bone structure upon rotation of the elongate member in a first direction and a second, opposite direction.

5. The surgical bone preparation instrument of claim 2, wherein the first and second blade members of the elongate member extend beyond the distal end of the sleeve member and are disposed adjacent to the at least one distractor member.

6. The surgical bone preparation instrument of claim 1, wherein the proximal end of the elongate member includes a gripping element.

7. The surgical bone preparation instrument of claim 6, wherein the gripping element is a knurled surface.

8. The surgical bone preparation instrument of claim 1, wherein the distal end of the sleeve member includes a stop member adapted to limit penetration of the instrument between adjacent bone structures.

9. The surgical bone preparation instrument of claim 8, wherein the stop member comprises a flange member that is oriented substantially perpendicular to a longitudinal axis of the instrument, the flange member extending radially outward from the sleeve member.

10. The surgical bone preparation instrument of claim 9, wherein the at least one distractor member comprises first and second opposed members that extend distally from the stop member, the opposed members being adapted to be disposed between adjacent bone structures for separating the adjacent bone structures by a predetermined distance.

11. The surgical bone preparation instrument of claim 10, wherein the first and second opposed members each include a tapered distal end to facilitate insertion of the first and second opposed members between adjacent bone structures.

12. The surgical bone preparation instrument of claim 1, further comprising a cutting template having a circumferential slot formed in the sleeve member and extending over a portion of a circumference of the sleeve member, and an engaging element extending from the elongate member and into the circumferential slot in the sleeve member, the cutting template being effective to limit rotation of the elongate member.

13. The surgical bone preparation instrument of claim 12, wherein the slot defines a cutting path extending over a range of between about 80° and 120° around a portion of the circumference of the sleeve member.

14. The surgical bone preparation instrument of claim 13, wherein the cutting path extends over a range of about 90° around a portion of the circumference of the sleeve member.

15. The surgical bone preparation instrument of claim 1, wherein the cutting surface of each of the first and second blade members is angularly oriented such that a proximal portion of the cutting surface is disposed a greater distance from a longitudinal axis of the elongate member than a distal portion of the cutting surface.

16. The surgical bone preparation instrument of claim 1, wherein the cutting surface of each of the first and second blade members is oriented parallel to a longitudinal axis of the elongate member.

17. A surgical bone preparation instrument, comprising:
a housing component having a proximal end and a distal end with a bore extending between the proximal and distal ends;
a distractor protruding distally from the distal end of the housing component and adapted to be disposed between adjacent bone structures; and
a rotatable cutting member, a portion of which is disposed within the bore of the housing component, the rotatable cutting member having a proximal handle portion and a distal cutting portion with at least one cutting element disposed thereon, the cutting element being adapted to remove only substantially diagonally opposed regions of bone from the adjacent bone structures.

18. The surgical bone preparation instrument of claim 17, wherein a portion of the rotatable cutting member is removably and replaceably disposed within the bore of the housing component.

19. The surgical bone preparation instrument of claim 17, wherein the rotatable cutting member has a body portion with proximal and distal ends and a longitudinal axis extending therebetween, and wherein the at least one cutting element comprises first and second blade members extending radially outward from the distal end of the body portion.

20. The surgical bone preparation instrument of claim 19, wherein the first and second blade members are adapted to remove a portion of the adjacent bone structures upon rotation of the elongate member in a first direction and in a second, opposite direction.

21. The surgical bone preparation instrument of claim 19, wherein the first blade member is opposed to and offset with respect to the second blade member.

22. The surgical bone preparation instrument of claim 21, wherein the first and second blade members each include at least one cutting surface angularly oriented such that a proximal portion of the cutting surface is disposed a greater distance from the longitudinal axis than a distal portion of the cutting surface.

23. The surgical bone preparation instrument of claim 22, wherein the at least one cutting surface of the first and second blade members are disposed radially outward from the body portion of the rotatable cutting member at a distance of between about 1 mm and 5 mm.

24. The surgical bone preparation instrument of claim 23, wherein the at least one cutting surface of the first and second blade members are disposed radially outward from the body portion of the rotatable cutting member at a distance of 2 mm.

25. The surgical bone preparation instrument of claim 17, wherein the distractor comprises first and second opposed members each having a proximal end and a distal end, the proximal end being mated to the housing component and the distal end being substantially bullet-shaped.

26. The surgical bone preparation instrument of claim 17, wherein the distal end of the housing includes a shoulder for preventing the housing from penetrating a space between the adjacent bone structures.

27. The surgical bone preparation instrument of claim 26, wherein the adjacent bone structures are vertebrae.

28. The surgical bone preparation instrument of claim 17, wherein the housing component is substantially cylindrical and includes a rotation limiting element defining a cutting path for the at least one cutting element.

29. The surgical bone preparation instrument of claim 28, wherein the rotation limiting element comprises a circumferential slot formed in the housing and extending over a portion of a circumference of the housing.

30. The surgical bone preparation instrument of claim 29, wherein the rotatable cutting member includes a pin member disposed on the rotatable cutting member and extending radially therefrom, the pin member adapted to be disposed within the circumferential slot in the housing.

31. The surgical bone preparation instrument of claim 17, wherein the cutting element includes at least one cutting surface angularly oriented such that a proximal portion of the cutting surface is disposed a greater distance from a longitudinal axis of the rotatable cutting element than a distal portion of the cutting surface.

32. The surgical bone preparation instrument of claim 17, wherein the cutting element includes at least one cutting surface oriented parallel to a longitudinal axis of the rotatable cutting element.

33. A method for preparing the surface of adjacent vertebral bodies, comprising:
providing a surgical bone preparation instrument having
a sleeve member with a proximal end, a distal end, and an inner lumen formed therein,
a distractor member extending distally from the distal end of the sleeve member and adapted to be disposed between adjacent bone structures, and
a rotatable cutting member, a portion of which is disposed within the inner lumen of the sleeve member, the rotatable cutting element having a proximal handle portion and a distal cutting portion with opposed first and second cutting elements disposed thereon, each of the first and second cutting elements having a longitudinally oriented cutting surface formed thereon,
inserting the distractor member of the surgical bone preparation instrument between adjacent vertebral bodies; and
rotating the rotatable cutting member over a predetermined cutting path to remove a portion of the surface of the adjacent vertebral bodies.

34. The method of claim 33, wherein the rotatable cutting member is rotated manually.

35. The method of claim 33, wherein the rotatable cutting member is rotated between about 80° and 120° in a first direction, and between about 80° and 120° in second, opposite direction.

36. The method of claim 33, wherein the rotatable cutting member is rotated about 90° in a first direction, and about 90° in second, opposite direction.

37. The method of claim 33, wherein the first cutting element is adapted to remove a portion of a first vertebral endplate, and the second cutting element is adapted to remove a portion of a second vertebral endplate, the first and second vertebral endplates being adjacent to each other.

38. The method of claim 37, wherein the removed portion of the first vertebral endplate is formed in the anterior region, and the removed portion of the second vertebral endplate is formed in the posterior region.

39. The method of claim 38, wherein the removed portion of the first vertebral endplate is formed in the first lateral half of the anterior region and the removed portion of the second vertebral endplate is formed in the second lateral half of the posterior region.

40. The method of claim 37, wherein each of the first and second cutting elements is adapted to remove between about 10% and 50% of the bone structure surface.

41. The method of claim 40, wherein each of the first and second cutting elements is adapted to remove about 25% of the bone structure surface.

42. A surgical bone preparation instrument, comprising:
a sleeve member having a proximal end, a distal end, and an inner lumen formed therein, the sleeve member having at least one distractor member protruding distally from the distal end and adapted to be disposed between adjacent bone structures; and
an elongate member at least partially rotatably disposed within the sleeve member, the elongate member having a proximal end and a distal end with a cutting means formed on a portion thereof, the cutting means being effective to remove only substantially diagonally opposed regions of bone from the adjacent bone structures.

43. The surgical bone preparation instrument of claim 42, wherein the cutting means includes at least one longitudinally extending cutting surface.

44. The surgical bone preparation instrument of claim 42, wherein the distal end of the sleeve member includes a stop member adapted to limit penetration of the instrument between adjacent bone structures.

45. The surgical bone preparation instrument of claim 44, wherein the at least one distractor member comprises first and second opposed members that extend distally from the stop member, the opposed members being adapted to be disposed between adjacent bone structures for separating the adjacent bone structures by a predetermined distance.

46. The surgical bone preparation instrument of claim 42, further comprising a cutting template having a circumferential slot formed in the sleeve member and extending over a portion of a circumference of the sleeve member, and an engaging element extending from the elongate member and into the circumferential slot in the sleeve member, the cutting template being effective to limit rotation of the elongate member.

47. The surgical bone preparation instrument of claim 46, wherein the slot defines a cutting path extending over a range of between about 80° and 120° around a portion of the circumference of the sleeve member.

48. The surgical bone preparation instrument of claim 47, wherein the cutting path extends over a range of about 90° around a portion of the circumference of the sleeve member.

* * * * *